United States Patent
Kuroda et al.

(10) Patent No.: US 7,908,824 B2
(45) Date of Patent: Mar. 22, 2011

(54) INDIVIDUAL PACKAGE OF ABSORBENT ARTICLE

(75) Inventors: Kenichiro Kuroda, Kagawa (JP); Wataru Yoshimasa, Kagawa (JP); Satoshi Nozaki, Kagawa (JP); Masahiro Kashiwagi, Kagawa (JP); Noritatsu Tamagawa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 225 days.

(21) Appl. No.: 12/142,479

(22) Filed: Jun. 19, 2008

(65) Prior Publication Data

US 2008/0276570 A1    Nov. 13, 2008

Related U.S. Application Data

(62) Division of application No. 10/256,231, filed on Sep. 26, 2002, now abandoned.

(30) Foreign Application Priority Data

Oct. 2, 2001   (JP) ................ 2001-306041
Sep. 24, 2002  (JP) ................ 2002-277280

(51) Int. Cl.
    *B65B 51/00*   (2006.01)
(52) U.S. Cl. ............ 53/416; 53/429; 53/116; 53/135.2
(58) Field of Classification Search ............ 53/411, 53/412, 415, 416, 429, 463, 477, 116, 131.1, 53/133.3, 133.4, 133.5, 135.2, 135.3, 375.9
See application file for complete search history.

(56) References Cited

U.S. PATENT DOCUMENTS

| 2,564,689 | A | * | 8/1951 | Harwood et al. | 604/366 |
| 2,772,181 | A | * | 11/1956 | Rogers et al. | 427/194 |
| 3,407,814 | A | * | 10/1968 | George et al. | 604/364 |
| 4,178,337 | A | | 12/1979 | Hall et al. | |
| 4,379,806 | A | * | 4/1983 | Korpman | 428/354 |
| 4,895,760 | A | * | 1/1990 | Barger | 428/332 |
| 5,413,568 | A | * | 5/1995 | Roach et al. | 604/358 |
| 5,462,166 | A | * | 10/1995 | Minton et al. | 206/440 |
| 5,681,306 | A | | 10/1997 | Goulait et al. | |

(Continued)

FOREIGN PATENT DOCUMENTS

JP        03-269145        11/1991

(Continued)

OTHER PUBLICATIONS

English Translation of Matsuoka et. JP 11-042248.

(Continued)

*Primary Examiner* — Paul R Durand
(74) *Attorney, Agent, or Firm* — Morrison & Foerster LLP

(57) ABSTRACT

An individual package of an absorbent article permits a base end of a tape to be bonded with sufficiently large bonding strength without complicating packaging process and increasing manufacturing cost. The absorbent article is wrapped by a package sheet having side edge portions and end edges, and one end edge is overlapped over the other end edge. The package sheet is sealed along the side edge portions, a base end of a tape is fixed on the surface of the package sheet located outside in an overlapping portion, and a free end of the tape extends across one end edge and is releasably adhered on the outer surface of the package sheet adjacent one end edge. The package sheet has a surface, on which the base end of the tape is fixed, the surface being smoothed by a smoothing process.

2 Claims, 8 Drawing Sheets

U.S. PATENT DOCUMENTS

| | | | | |
|---|---|---|---|---|
| 5,694,739 A | * | 12/1997 | Mattingly, III | 53/429 |
| 6,036,679 A | * | 3/2000 | Balzar et al. | 604/387 |
| 6,168,582 B1 | * | 1/2001 | Hasegawa | 604/385.02 |
| 6,489,533 B2 | | 12/2002 | Imai et al. | |

FOREIGN PATENT DOCUMENTS

| | | |
|---|---|---|
| JP | 05048924 U | 6/1993 |
| JP | 8500502 | 1/1996 |
| JP | H08-500502 | 1/1996 |
| JP | 09220254 | 8/1997 |
| JP | 11-042248 | 2/1999 |
| JP | 2001010606 | 1/2001 |
| JP | 2001-198160 A1 | 7/2001 |
| WO | 94/04111 | 3/1994 |
| WO | WO-9404111 | 3/1994 |
| WO | 99/26574 A1 | 6/1999 |
| WO | 01/24748 A1 | 4/2001 |

OTHER PUBLICATIONS

Kuroda, K. et al., U.S. Office Action mailed Mar. 9, 2005, directed to U.S. Appl. No. 10/256,231; 12 pages.

Kuroda, K. et al., U.S. Office Action mailed Aug. 22, 2005, directed to U.S. Appl. No. 10/256,231; 13 pages.

Kuroda, K. et al., U.S. Office Action mailed Jan. 31, 2006, directed to U.S. Appl. No. 10/256,231; 12 pages.

Kuroda, K. et al., U.S. Office Action mailed May 19, 2006, directed to U.S. Appl. No. 10/256,231; 11 pages.

Kuroda, K. et al., U.S. Office Action mailed Nov. 17, 2006, directed to U.S. Appl. No. 10/256,231; 12 pages.

Kuroda, K. et al., U.S. Office Action mailed Aug. 9, 2007, directed to U.S. Appl. No. 10/256,231; 8 pages.

Kuroda, K. et al., U.S. Office Action mailed Feb. 25, 2008, directed to U.S. Appl. No. 10/256,231; 8 pages.

* cited by examiner

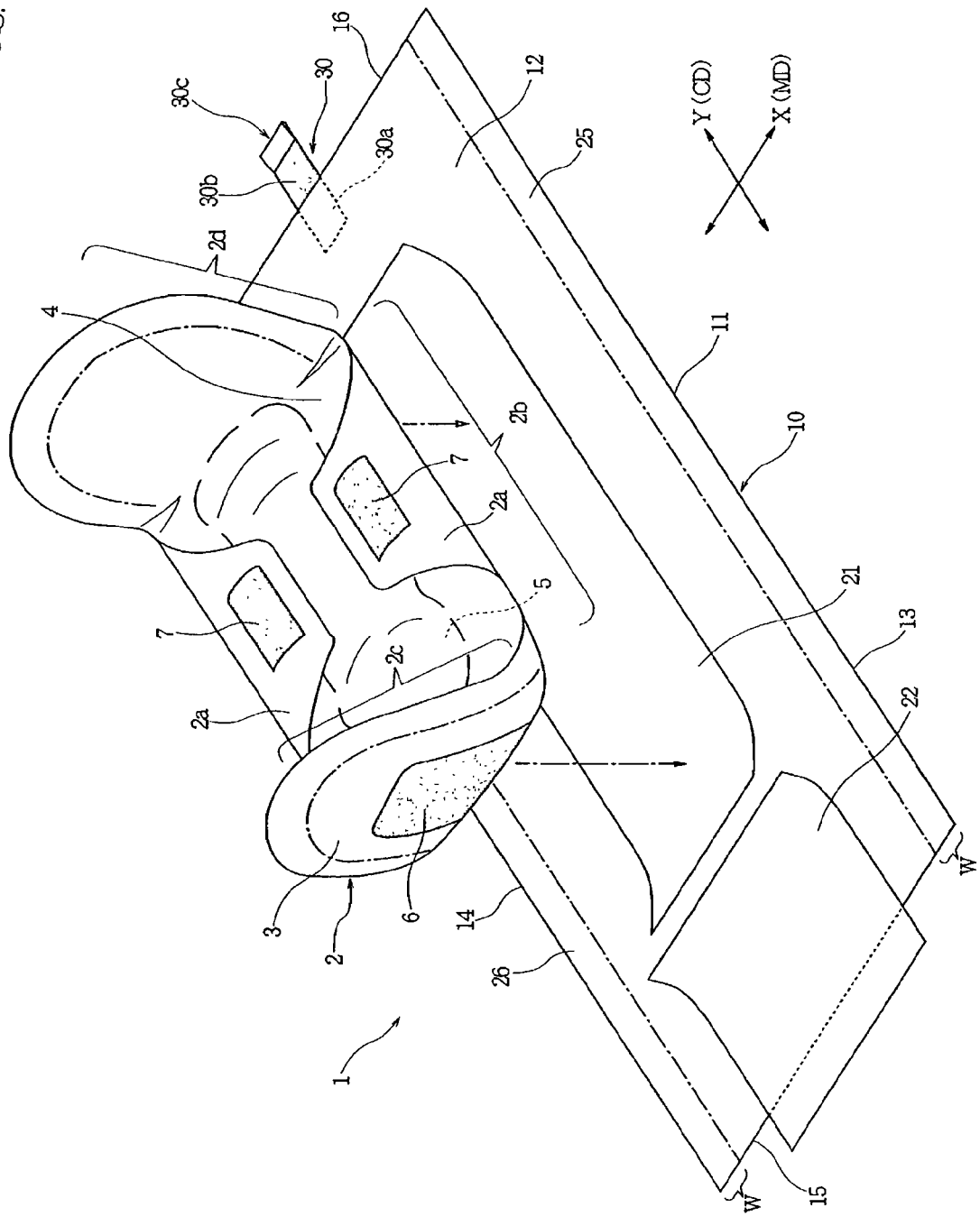

INDIVIDUAL PACKAGE OF ABSORBENT ARTICLE

CROSS-REFERENCE TO RELATED APPLICATION

This application is a divisional application of U.S. patent application Ser. No. 10/256,231, filed on Sep. 26, 2002 and claiming priority under 35 U.S.C. §119 to Japanese Patent Application No. 2002-277280, filed on Sep. 24, 2002, and Japanese Patent Application No. 2001-306041, filed on Oct. 2, 2001, the disclosures of which are incorporated herein by reference in their entireties.

BACKGROUND OF THE INVENTION

1. Field of the Invention

The present invention relates to an individual package, in which an absorbent article, such as sanitary napkin, panty liner, sanitary tampon, incontinence pad, disposable diaper and so forth is individually packed.

2. Description of the Related Art

For example, an absorbent article, such as sanitary napkin or the like, is individually packed into an individual package. Conventionally, a package sheet of the individual package is formed from a polyethylene film or the like. It is a typical structure that side portions of the package sheet are heat sealed in a condition wrapping the absorbent article.

However, the package sheet formed from a resin film, such as polyethylene film and so forth may generate husky (or crinkly) noise upon handling due to friction with a packaging film upon opening the package and taking out the absorbent article. This is true even in the case where the individual package is taken out from a porch, is carried in hand, or is carried in a pocket of pants or skirt. On the other hand, the resin films are firmly bonded by heat seal to cause difficulty in opening the package for large anti-peeling resistance upon peeling the heat sealed portion. Furthermore, since the large force is required in opening the package, high husky or crinkly noise can be generated. As a result, uncomfortable feeling may be caused for the fear if unpacking of the sanitary napkin or the like can be perceived by surrounding people. On the other hand, the package sheet formed from polyethylene film is not always preferably in terms of product form due to stiff external appearance of the individual package. Furthermore, since the polyethylene film is heat sealed, gas-tightness of the sealed individual package becomes excessively high to cause bursting of the package sheet at the heat sealed portion when large external force is applied during carrying.

In view of the inconvenience set forth above, there have been proposed individual packages having the package sheets formed from non-woven fabric, such as those disclosed in Japanese Unexamined Patent Publication (Kokai) No. Heisei 11-42248, for example. In case of individual package of the absorbent article employing the package sheet of non-woven fabric, husky noise to be generated by such package sheet upon unpacking is small. Furthermore, since bonding area of the heat sealed portion is substantially small, peeling sound upon unpacking the heat sealed portion becomes small. Also, the non-woven fabric package sheet may provide soft external appearance for the individual package to attain better appearance. Furthermore, when large external force is applied, air in the individual package may escape through gaps between fibers of the non-woven fabric so as not to cause bursting during carrying.

In the individual package, it is typical that a base end portion of a tape is fixed on a surface of the package sheet portion located at the outermost position in the condition where the end edges of the package sheet are overlapped on an outer surface of the package sheet, and a free end of the tape is extended beyond the end edge of the package sheet and is peelably bonded on the surface of the package sheet adjacent to the end edge. Upon unpacking of the individual package of the absorbent article, the free end of the tape is peeled from the surface of the package sheet adjacent to the end edge, and the package sheet on which the base end of the tape is fixed is lifted up together with the tape, thereby the heat sealed portion can be peeled to easily unpack the individual package.

However, in the package sheet formed from the non-woven fabric, fibers appear on the outer surface in random fashion. Therefore, in a fixing portion between the fibers on the surface of the package sheet and the base end of the tape, bonding area becomes substantially small to lower fixing strength. Therefore, when the free end of the tape is peeled from the surface of the package sheet adjacent to the end edge and lifted up, the base end of the tape can be easily peeled from the surface of the package sheet. Accordingly, once the entire tape is peeled and removed, inconvenience is encountered in handling upon unpacking the individual package.

On the other hand, in case of the individual package of the sanitary napkin, upon wearing the unpacked sanitary napkin, the unpacked package sheet may be used for wrapping the used sanitary napkin. Then, the free end of the tape extending from the end edge of the package sheet is bonded on the outer surface of the package sheet for disposal. However, if the base end of the tape is not firmly fixed on the package sheet, when the free end of the tape is pulled for firmly wrapping the used sanitary napkin by the package sheet, the base end may be peeled off the outer surface of the package sheet to cause difficulty in wrapping the used sanitary napkin for disposal.

In order to solve the problem set forth above, an approach is considered to use an adhesive having high bonding strength in fixing the base end of the tape on the surface of the package sheet, and to use an adhesive having lower bonding strength in bonding the free end of the tape on the surface of the package sheet at the position adjacent to the end edge of the package sheet. In another approach, greater thickness may be provided for the adhesive at the portion where the base end of the tape is bonded on the surface of the package sheet, and smaller thickness may be provided for the adhesive at the portion where the free end of the tape is bonded on the surface of the package sheet. However, using two kinds of adhesives in bonding the tape on the package sheet or varying application amounts at different positions inherently make packaging process complicate to increase manufacturing cost. Furthermore, the adhesive used for fixing the base end of the tape may run out toward the position of the package sheet on which the free end of the tape is bonded, to fix the free end of the tape with excessively large bonding strength on the package sheet to cause difficulty in unpacking.

SUMMARY OF THE INVENTION

The present invention has been worked out in view of the shortcoming in the prior art set forth above. It is therefore an object of the present invention to provide an individual package of an absorbent article which permits a base end of a tape to be bonded on a package sheet with sufficiently large bonding strength without complicating packaging process and increasing manufacturing cost.

According to the first aspect of the present invention, an individual package of an absorbent article, wherein, in a condition where an absorbent article is wrapped by a package sheet having mutually opposing side edge portions and mutually opposing end edges, one end edge is overlapped over the other end edge with placing the one end edge of the package sheet outside for forming an overlapping portion, and the package sheet is releasably sealed along the side edge portions, a base end of a tape is fixed on the surface of the package sheet located outside in the overlapping portion, and a free end of the tape extends across the one end edge and is releasably adhered on the outer surface of the package sheet adjacent the one end edge, comprises:

the package sheet having a surface, on which the base end of the tape is fixed, the surface being smoothed by a smoothing process.

By smoothing the surface of the package sheet formed from fibrous structure, the base end of the tape can be certainly and firmly secured on the surface of the package sheet.

Preferably, the package sheet may be formed from a non-woven fabric.

In such case, the side edge portions of the package sheet in a plurality of layers may be bonded with each other, and the smoothed region may be located at a position away from the bonded portion of the package sheet.

When the smoothed region is formed at the position away from the bonded portion, softness of the package sheet of the non-woven fabric in the bonded portion can be maintained to maintain the force required for opening the package by peeling the package sheet in the bonded portion small to make husky or crinkly noise upon opening the individual package small.

The smoothing process may be to increase fiber density of the surface by pressurizing the surface of the package sheet. Further preferably, the smoothing process may be to increase fiber density of the surface by heating and pressurizing the surface of the package sheet.

As set forth above, by pressurizing or by pressurizing and heating, the package sheet can be easily smoothed.

In the alternative, the smoothing process may be to form a resin film on an outer surface of the package sheet.

By coating or laminating the resin film on the outer surface of the package sheet of fibrous structure, the surface of the package sheet can be easily smoothed.

According to the second aspect of the present invention, an individual package of an absorbent article, wherein, in a condition where an absorbent article is wrapped by a package sheet having mutually opposing side edge portions and mutually opposing end edges portions, one end edge portion is overlapped over the other end edge portion with placing the one end edge portion of the package sheet outside for forming an overlapping portion, and the package sheet is releasably sealed along the side edge portions, a base end of a tape is fixed on the surface of the package sheet located outside in the overlapping portion, and a free end of the tape extends across the one end edge portion and is releasably adhered on the outer surface of the package sheet adjacent the one end edge portion, comprises:

a base end of the tape being adhered on a surface of the package sheet, and the package sheet and the base end of the tape are pressurized together.

By pressuring the tape and the package sheet after bonding them, the adhering strength of the tape can be increased.

The base end of the tape to be firmly fixed to the surface of the package sheet and the free end of the tape releasably adhered on the outer surface of the package sheet adjacent one end edge portion may be applied the same adhesive.

Since the portion of the package sheet is smoothed in the portion, on which the base end of the tape is adhered, the tape and the package sheet is firmly adhered with sufficiently large adhering force. Accordingly, in the condition where the same adhesive is applied to both ends of the tape, the base end can be firmly adhered on the package sheet, and the free end of the tape can be releasably adhered on the adjacent package sheet. By applying the same adhesive on both ends of the tape, the tape can be easily manufactured at low cost.

According to the third aspect of the present invention, an individual package of an absorbent article comprises:

a package sheet having first and second side edges extending longitudinally and first and second end edges located at both longitudinal ends of the package sheet;

an absorbent article being wrapped by the package sheet;

a first wrapping portion of the package sheet including the first end edge and folded over the absorbent article;

a second wrapping portion of the package sheet including the second end edge and folded over the absorbent article overlapping with the first wrapping portion with placing the first wrapping portion in outermost position;

the first and second wrapping portions being joined or bonded with a center portion of the package sheet located between the first and second wrapping portions along both of the first and second side edges;

a tape having an uniformly applied adhesive layer and having first end portion and a second end portions;

a smoothed portion formed in the first wrapping portion for firmly adhering receiving the first end portion of the tape for firmly adhering the same; and the tape extending from the first end portion of the tape firmly adhered on the first wrapping portion extending across the first end edge so that the second end portion thereof is releasably adhered on the second wrapping portion.

According to the fourth aspect of the present invention, a package sheet for packing an absorbent article, formed from fibrous sheet, and having first and second side edges extending longitudinally and first and second end edges located at both longitudinal ends of the package sheet, comprises:

a first wrapping portion of the package sheet including the first end edge and folded over the absorbent article;

a second wrapping portion of the package sheet including the second end edge and folded over the absorbent article overlapping with the first wrapping portion with placing the first wrapping portion in outermost position;

the first and second wrapping portions being joined or bonded with a center portion of the package sheet located between the first and second wrapping portions along both of the first and second side edges, the first and second wrapping portions being fixed by a tape having an uniformly applied adhesive layer and having a first end portion and a second end portion;

a smoothed portion formed in the first wrapping portion and receiving the first end portion of the tape for firmly adhering the same; and the second wrapping portion receiving the second end portion of the tape for releasably adhering the same.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings:

FIG. 2 is a perspective view of the individual package of the absorbent article of the present invention illustrated in developed condition;

FIGS. 12A and 12B are diagrammatic illustrations showing an image processed surface of non-woven fabric, wherein FIG. 12A shows the surface of the non-woven fabric not smoothed and FIG. 12B shows the smoothed surface of the non-woven fabric.

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure is not shown in detail in order to avoid unnecessary obscurity of the present invention.

Figure 1:
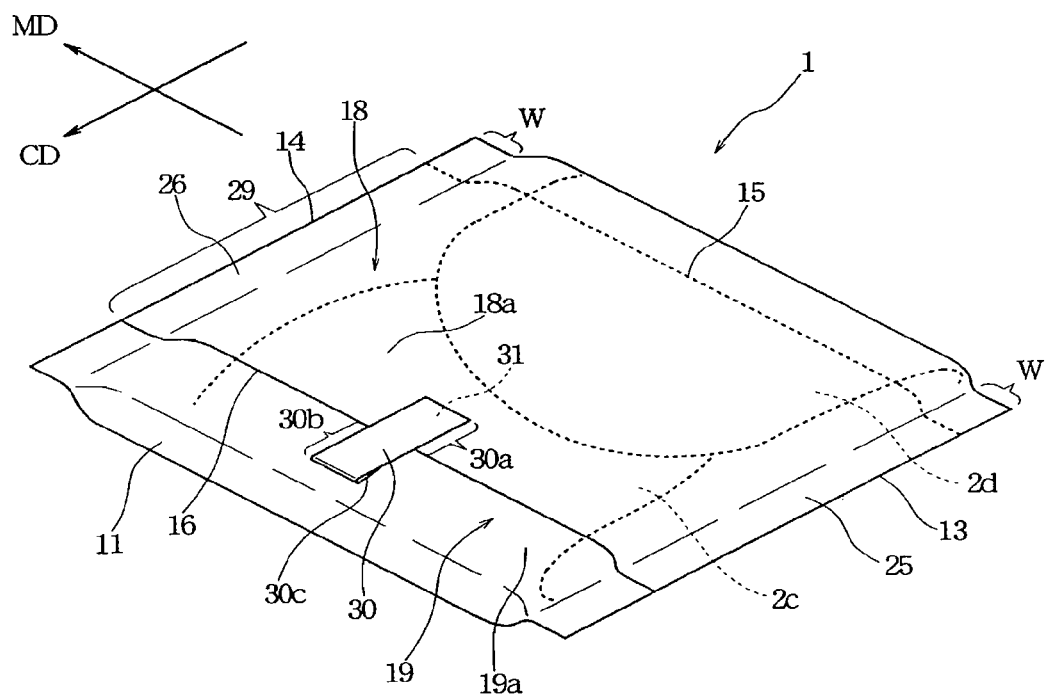
FIG. 1 is a perspective view of an individual package of an absorbent article according to the present invention.
Figure 3A:
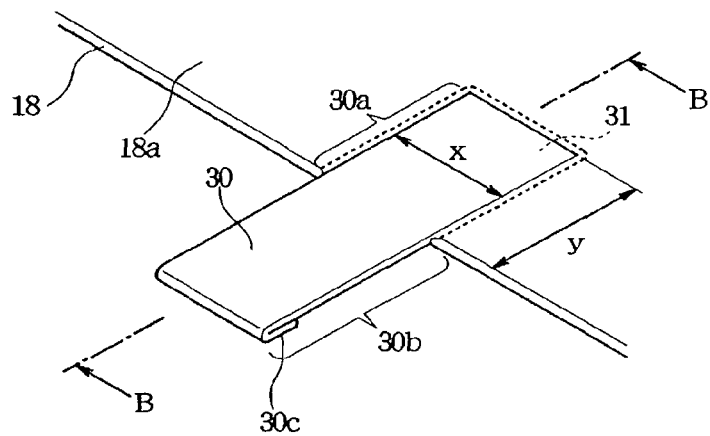
FIG. 3A is a partial perspective view of the individual package.
Figure 3B:
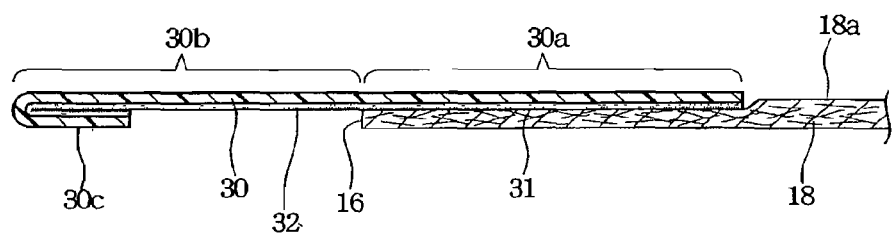
FIG. 3B is a section taken along line B-B of FIG. 3A.

FIG. 1 is a perspective view of an individual package of an absorbent article according to the present invention, FIG. 2 is a perspective view of the individual package of the absorbent article of the present invention illustrated in developed condition, FIG. 3A is a partial perspective view of the individual package, and FIG. 3B is a section taken along line B-B of FIG. 3A.

In an individual package 1 shown in FIGS. 1 and 2, each individual sanitary napkin 2 is wrapped by a package sheet 10 one-by-one.

The package sheet 10 has a first surface 11 to be placed outside of the individual package 1 shown in FIG. 1 and a second surface 12 to be placed inside of the individual package 1. At least the first surface 11 of the package sheet 10 is formed with a fibrous structure. Preferably, the entire package sheet 10 is formed with the fibrous structure.

For example, in the shown embodiment, a spun-bonded non-woven fabric is exposed on the first surface 11 and the spun-bonded non-woven fabric is also exposed on the second surface 2. Between the spun-bonded non-woven fabrics respectively exposed on the first and second surfaces 11 and 12, a meltblown non-woven fabric is sandwiched to form a three-layer structure.

The spun-bonded non-woven fabric is fabricated by forming continuous fiber by extruding thermoplastic molten resin through a nozzle of spinner and heat-fusing the continuous fiber between heat rollers. The thermoplastic continuous fiber may be a single fiber of PE (polyethylene), PP (polypropylene), PET (polyethylene terephthalate), graft polymer of PE and PP or bicomponent fiber of sheath-core structure including PP or PET in core portion and PE in sheath portion. The fineness of the continuous fiber forming the spun-bonded non-woven fabric is in a range of about 1.1 to about 6.6 dtex.

The meltblown non-woven fabric is fabricated by extruding thermoplastic molten resin through a fine nozzle of a spinner, blowing hot air around the fine nozzle to form extremely fine continuous or non-continuous fiber, and heat-fusing extremely fine fibers by the hot rollers and so forth. Thermoplastic fine fiber may be a single fiber of PE, PP and PET, graft polymer of PE and PP or bicomponent fiber of sheath-core structure including PP or PET in core portion and PE in sheath portion. The meltblown non-woven fabric formed from fine fibers has high fiber density with smaller gap to exhibit superior barrier ability for dirt in the atmosphere and water resistance. Fineness of the fine fiber forming the meltblown non-woven fabric is in a range of about 0.11 to about 0.66 dtex.

In the condition where the spun-bonded non-woven fabrics on the sides of the first and second surfaces 11, 12 and the meltblown non-woven fabric disposed between the spun-bonded non-woven fabrics are laminated, predetermined emboss pattern is formed for partially heat-fused portions by pressurization and heating. Thus, the laminated non-woven fabrics are integrated by the partially heat-fused portions.

A basis weight of the entire package sheet 10 is preferably in a range of 10 to 100 g/m$^2$. When the basis weight is smaller than 10 g/m$^2$, the strength of the package sheet 10 becomes low to potentially cause rupture of the individual package 1. On the other hand, when the basis weight is in excess of 100 g/m$^2$, the package sheet 10 becomes excessively thick to be excessively stiff entirely in the condition of the individual package 1.

The package sheet 10 is formed from composite material of non-woven fabrics to hardly generate rustling sound upon unpacking. On the other hand, upon peeling the heat sealed portion, peeling sound becomes small.

The package sheet 10 has both side edge portions 13 and 14 extending in a longitudinal direction (Y direction in FIG. 2), and first and second end edges 15 and 16 located at front and rear ends in the longitudinal direction. The side edge portions 13 and 14 provide longer edges and the first and second end edges 15 and 16 provide shorter edges to form rectangular package sheet 10.

The sanitary napkin 2 to be wrapped by the package sheet 10 includes a liquid impermeable back sheet 3, a liquid permeable surface sheet 4 and an absorbent layer 5 disposed between the back sheet 3 and the surface sheet 4. The back sheet 3 and the surface sheet 4 are bonded together along the circumference surrounding the absorbent layer 5. In a center portion 2b of the sanitary napkin 2, wing portions 2a are extended laterally.

On the surface of the back sheet 3, a main body side adhesive layer 6 is provided. On the other hand, on the surface of the back sheet 3 forming the wing portions 2a, wing side adhesive layers 7 are provided. The adhesive layers 6 and 7 are pressure sensitive adhesive such as a rubber type, having repeatedly adhering ability to adhering object with appropriate adhering strength.

As shown in FIG. 2, on the second surface 12 oriented toward inside of the package sheet 10, a first release sheet or release paper 21 and a second release sheet or release paper 22 are fixed. Each of these release sheets 21 and 22 is formed from a synthetic resin film, tissue paper, laminated sheet, in which a film is laminated on the surface of a paper or non-woven fabric. On the surface of each release sheet 21, 22, silicon or fluorinated resin is applied and provided heat curing, UV curing or EB treatment to form a release surface to enable repeatedly peeling and adhering to the adhesive layers 6 and 7 of the sanitary napkin 2.

In the manufacturing method of the individual package 1, a strip form non-woven fabric to be the package sheet 10 is supplied continuously in MD direction shown in FIG. 2. The release sheets 21 and 22 are fitted on the surface of the strip form non-woven fabric. The sanitary napkin is mounted on the release sheets 21 and 22. Then, the non-woven fabric and the sanitary napkin 2 are folded into the shape shown in FIG. 1. Thereafter, the mating portion of the non-woven fabric is heat sealed. Subsequently, the non-woven fabric is cut to separate each individual package 1. The supply direction (MD) of the strip form non-woven fabric is X direction, and the Y direction perpendicular to the X direction is CD as shown in FIG. 2.

Next, the folded structure of the completed individual package 1 will be described. As shown in FIG. 2, in the condition where the main body side adhesive layer 6 formed on the back sheet 3 of the sanitary napkin 2 is fitted on the first release sheet 21 secured on the inner surface of the package sheet 10, a front portion 2c of the sanitary napkin 2 is sandwiched between a non-adhered portion of the second release sheet 22 and the package sheet 10. When the package sheet 10 and the front portion 2c are folded on the center portion 2b, the second release sheet 22 is fitted on the wing side adhesive layers 7. Furthermore, a rear portion 2d of the sanitary napkin 2 and the package sheet 10 are folded together overlapping on the front portion 2c.

As a result, as shown in FIG. 1, in the condition where the first end edge 15 of the package sheet 10 is sandwiched between the center portion 2b and the rear portion 2d of the sanitary napkin 2, the package sheet 10 is placed thereover to place the second end edge 16 of the package sheet 10 at the uppermost position. Here, a portion where the package sheet 10 is stacked sandwiching a part of the sanitary napkin 2 between the first end edge 15 and the second end edge 16 of the package sheet 10 will be referred to as an overlapping portion 29.

In strip form seal regions 25 and 26 extending along the side edge portions 13 and 14 of the package sheet 10 and having a width W, mutually mating portions of the package sheet 10 are pressurized and heated for fuse-bonding the mating portions of the package sheet 10 to form heat-sealed portions. Preferably, the heat-seal portions are in a form of plurality of dots distributed in respective seal regions 25 and 26.

A surface of an upper portion 18 of the package sheet 10 located at the outermost position in the overlapping portion 29 is identified by the reference numeral 18a. On the other hand, a surface of a lower portion 19 of the package sheet 10 mating with the upper portion 18 is identified by the reference numeral 19a.

In the individual package 1, from the surface 18a of the upper portion 18 of the package sheet 10 to the surface 19a of the lower portion 19 of the package sheet 10, a tape extending across the second end edge 16 is adhered. The tape 30 includes a base end portion fixed on the surface 18a by adhesion and serving as a fixed portion 30a, and a free end portion fixed on the surface 19a by adhesion and serving as a releasably adhering or bonding portion 30b. A region where the fixed portion 30a of the tape and the surface 18a of the package sheet 10 overlap, is a fixed region 31.

As shown in FIG. 3A, assuming that the width of the tape 30 is x and the overlapping length of the overlapping portion of the tape 30 and the surface 18a is y, the area of the fixed region 31 is (x×y).

The tape 30 is formed from a single layer film such as a polypropylene film, polyethylene film and the like, or a multilayer film laminated a plurality of kinds of resin films. As shown in FIG. 3B, on the lower surface of the tape 30, a pressure sensitive adhesive layer 32 is formed. The pressure sensitive adhesive layer 32 is formed of the same material and the same application amount (the same thickness and the same basis weight) over the entire length of the tape from the fixed portion 30a to the releasably adhering portion 30b of the tape 30.

The pressure sensitive adhesive layer 32 is typically formed from a rubber type or polyester type elastomer, a hot melt type adhesive essentially containing thermoset resin, and so forth.

In the embodiment shown in FIGS. 1 to 3, over the entire area of the fixed region 31, the surface 18a of the package sheet 10 is provided a smoothing process. The smoothing process is performed before fitting the tape 30 by pressurizing an area within the fixed region 31 or an area wider than the fixed region 31. By the pressurization process, the density of the fibers is increased in the surface 18a of the package sheet 10 to increase the number of fibers in the same surface or in one plane. As a result, effective contact area with the fixed portion 30a of the tape 30 is increased to achieve greater adhering force.

As further preferred smoothing process, in the fixed region 31 or in the area wider than the fixed region 31, the package sheet 10 is locally pressurized and heated. A heating temperature at this time is preferably higher than a softening point of the resin forming the fibers and lower than a melting point of the resin. By heating process, the resin on the surface of the fibers appearing on the outer surface of the package sheet 10 is softened to smooth the resin surface, and by pressurization process, the outer surface of the package sheet 10 is smoothed. Therefore, the fixed portion 30a of the tape 30 can be firmly fixed on the package sheet 10.

It should be noted that the smoothing process can be performed after adhering the fixed portion 30a of the tape 30 on the surface 18a of the package sheet 10. In this case, the package sheet 10 and the fixed portion 30a of the tape 30 are pressurized together or pressurized and heated. Thus, the surface 18a of the package sheet 10 can be smoothed in the fixed region 31 and the fixed portion 30a of the tape 30 can be further firmly fixed on the package sheet 10.

As shown in FIG. 3B, a part of the tip end of the adhering portion 30b of the tape 30 is folded and maintained in folded condition by the pressure sensitive adhesive layer 32 to form a grip portion 30c.

In the individual package shown in FIG. 1, in the condition where the fixed portion 30a of the tape 30 is firmly adhered on the surface 18a of the upper portion 18 of the package sheet 10 at the outermost position in the overlapping portion 29, the adhering portion 30b of the tape 30 extending across the second end edge 16, is adhered on the surface 19a of the package sheet 10, (which the surface 19a is not subject to smoothing process) by the pressure sensitive adhesive layer 32.

On the surface 19a, since the fibers forming the non-woven fabric are randomly oriented, the bonding area between the adhering portion 30b of the tape 30 and the surface 19a becomes substantially small. Accordingly, when the grip portion 30c at the tip end of the adhering portion 30b is gripped by the finger and is pulled up, the adhering portion 30b is relatively easily peeled off the surface 19a.

On the other hand, in the fixed region 31, the surface 18a of the package sheet 10 and the fixed portion 30a of the tape 30 are firmly adhered. Therefore, when the adhering portion 30b is lifted up, the fixed portion 30a of the tape 30 and the upper portion 18 of the package sheet 10 are not easily peeled off to be lifted up together with the tape 30. By lifting up the upper portion 18 of the package sheet 10, heat seal of the package sheet 10 in the strip form seal regions 25 and 26 is broken. Then, by gripping and lifting up the first end edge 15 of the package sheet 10, heat seal of the package sheet 10 in the strip form seal regions 25 and 26 is further broken to permit unpacking of the sanitary napkin 2 as shown in FIG. 2.

On the other hand, upon wearing of the unpacked sanitary napkin 2 replacing for the used sanitary napkin, the used sanitary napkin can be wrapped with the opened package sheet 10. At this time, the package sheet 10 is wrapped around the used sanitary napkin from the first end edge 15, and is fixed by adhering the adhering portion 30b of the tape 30 extending from the second end edge 16 at the trailing end, on the outer surface of the package sheet 10. Thus, the used sanitary napkin can be disposed with wrapping in the package sheet 10.

At this time, since the fixed portion 30a of the tape 30 is firmly adhered on the surface of the package sheet 10, the fixed portion 30a of the tape 30 will not be peeled off the surface of the package sheet 10 even if the grip portion 30c of the tape 30 is pulled with large force upon wrapping the used sanitary napkin.

Here, preferred smoothness of the surface of the non-woven fabric in the fixed region 31 subjecting to smoothing process in the package sheet 10 for bonding the tape 30, is greater than or equal to 50%. If the smoothness is less than 50%, bonding strength between the surface of the smoothed package sheet 10 and the fixed portion 30a of the tape 30 becomes too small. Further preferred smoothness is greater than or equal to 65%. Here, the smoothness is derived by picking up an image of the surface of the package sheet 10 or a predetermined measuring range of the surface performed smoothing process of the package sheet by means of a CCD camera, such as "teli CS5850" (tradename), manufactured by Tokyo Electronic Industry Kabushiki Kaisha, binarizing the image using an image analyzing software, such as "Image Hyper II Ver. 3.2" available from Kabushiki Kaisha Interfect, and deriving an area ratio of the smooth portion from the binarized image. By this, the area ratio of the fibrous area located at the surface of the package sheet or the portion appearing on the surface formed into a film by crushing the fibers is derived.

Figure 12A:
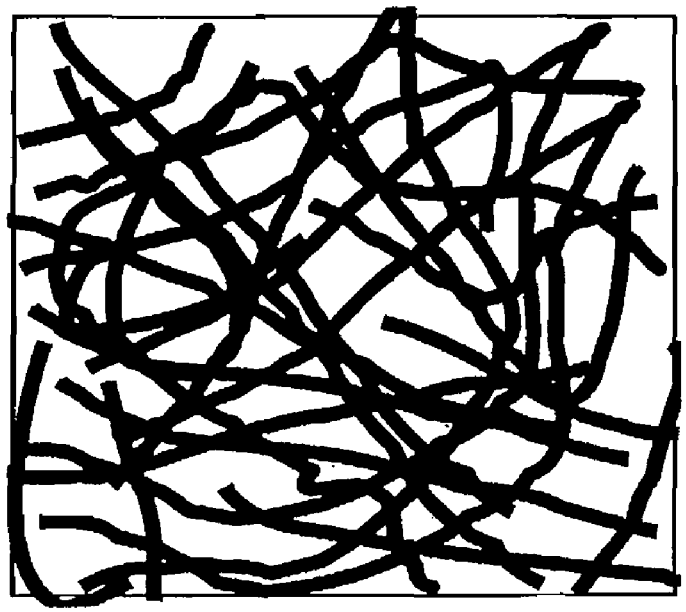
Figure 12B:

FIGS. 12A and 12B diagrammatically show one example of the binarized image in the measurement range. The surface of the non-woven fabric not subject to smoothing process appears as shown in FIG. 12A, whereas the smoothed surface of the non-woven fabric appears as shown in FIG. 12B. A ratio of the area of the portion binarized and shown in dark color appearing in each image versus the area of the measurement range is referred to as smoothness.

On the other hand, it is preferred that the package sheet 10 has a breaking strength in CD greater than or equal to 3N per 25 mm width, and a tear strength of the package sheet 10 in CD is greater than or equal to 2.5N. When the breaking strength and the tear strength in CD of the package sheet are greater than or equal to the foregoing values, unwanted rupture of the package sheet 10 can be successfully prevented upon lifting up the package sheet 10 together with the fixed portion 30a on unpacking by pulling the tape 30, or upon adhering the adhering portion 30b by pulling the tape 30 on wrapping the used sanitary napkin with the package sheet 10.

Figure 4:
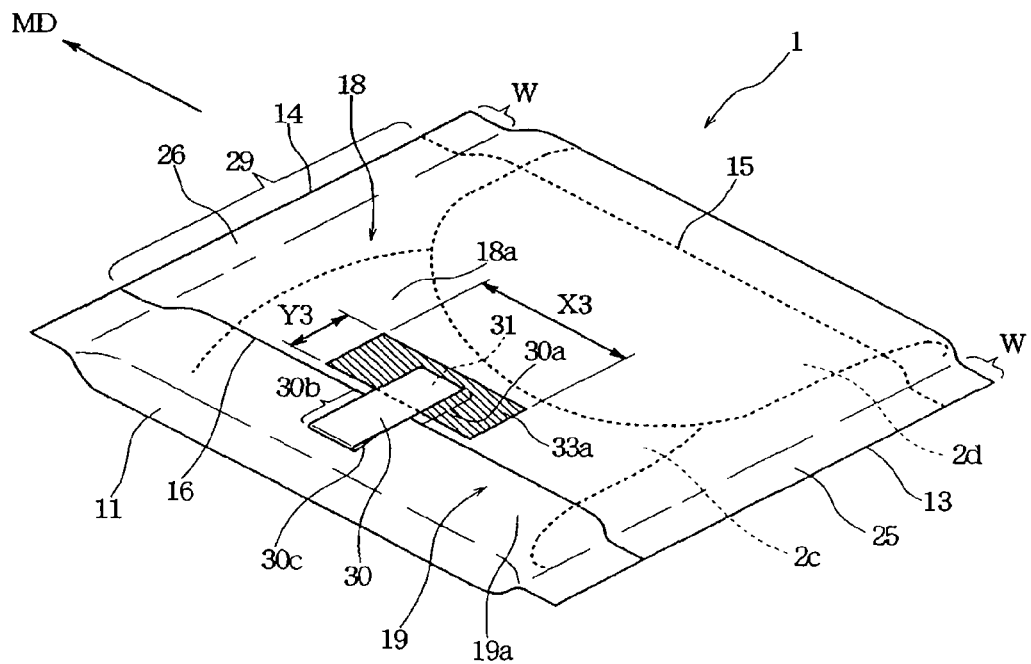
FIG. 4 is a perspective view showing one embodiment of a smoothed region in the individual package.
Figure 5:
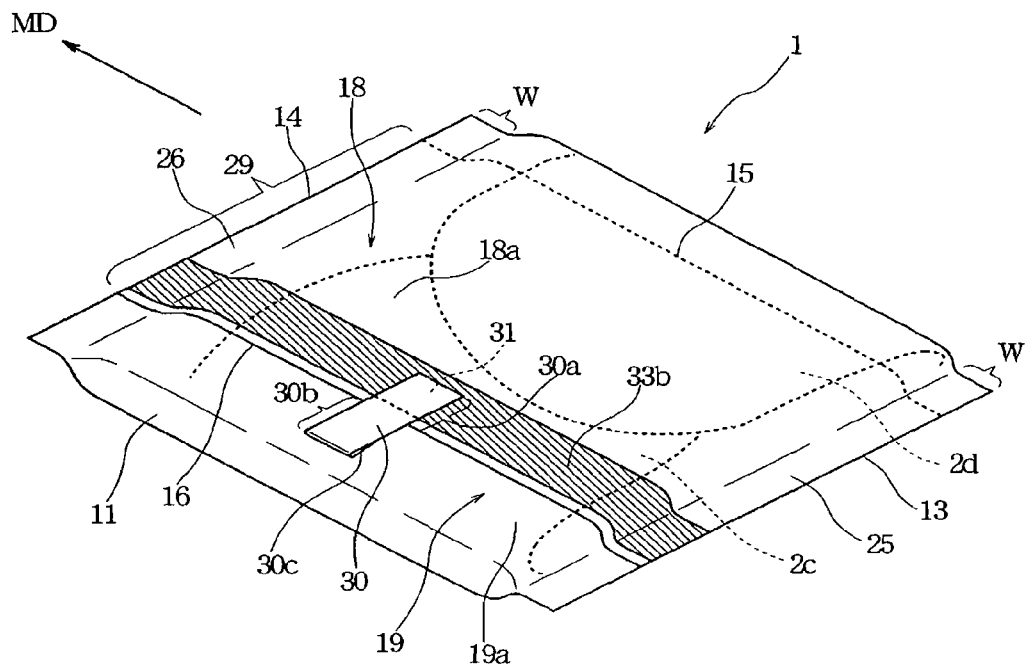
FIG. 5 is a perspective view showing another embodiment of the smoothed region in the individual package.
Figure 6:
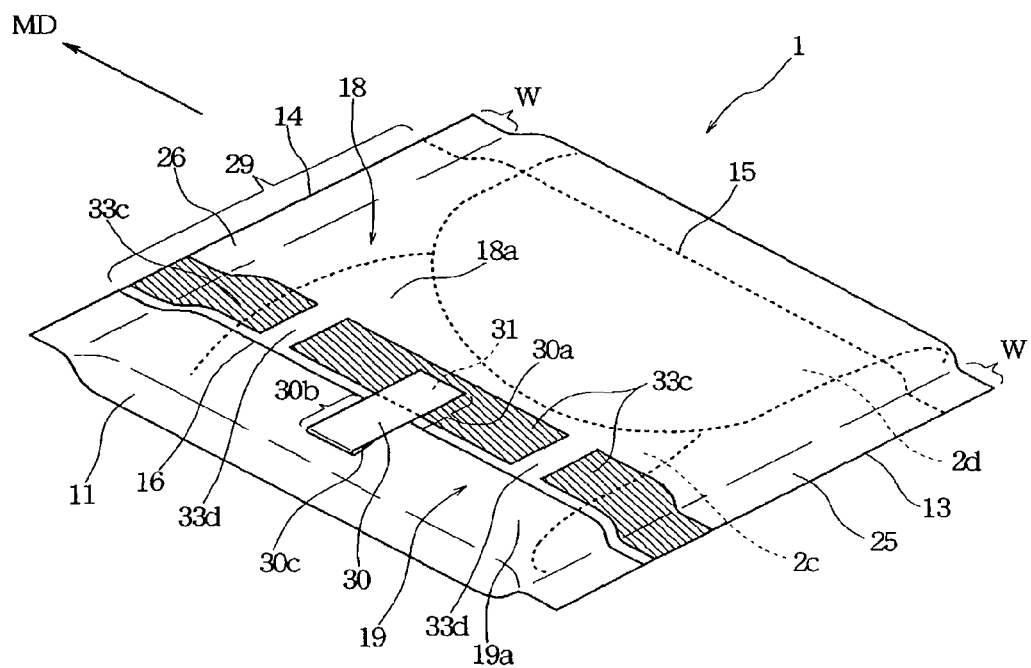
FIG. 6 is a perspective view showing a further embodiment of the smoothed region in the individual package.

Next, FIGS. 4 to 6 respectively show examples of regions to be subject to smoothing process.

In FIG. 4, a region subject to smoothing process is identified by the reference numeral 33a. In the shown example, the region 33a is formed into a stripe shape extending in MD direction. The length of the region 33a in the direction of MD is greater than the width x of the tape 30. In FIG. 5, a region subject to smoothing process is identified by the reference numeral 33b. The region 33b is formed into a stripe shape extending over the entire length in the direction of MD on the surface 18a of the package sheet 10. In FIG. 6, a region subject to smoothing process is identified by the reference numeral 33c. In this region 33c, on the surface 18a of the package sheet 10, a predetermined length of strip form smoothed region extending in the direction of MD is formed. The stripe form region 33c is separated by non-processed portions 33d provided with a given pitch.

The regions 33a, 33b and 33c shown in FIGS. 4 to 6 will be formed through the following processes.

In the manufacturing process of the individual package 1, a strip form non-woven fabric is continuously fed in the direction MD. By contacting a pressure roller or a pressure and heating roller onto the strip form non-woven fabric, the stripe form smoothed regions 33a, 33b and 33c extending in the direction MD can be formed on the non-woven fabric. After adhering the fixed portion 30a of the tape 30 onto the smoothed region 33a, 33b or 33c, the process is followed by the adhering process of the release sheets 21 and 22 to adhere the release sheets on the package sheet 10. After adhering the release sheets 21 and 22 on the package sheet 10, the sanitary napkin 2 is placed on the release sheets 21 and 22. Then, the sanitary napkin 2 and the package sheet 10 are folded and heat seal is provided in the strip form seal regions 25 and 26. Then, by cutting the non-woven fabric, the individual package 1 shown in FIG. 1 can be obtained.

As set forth above, by forming the stripe form smoothed regions 33a, 33b and 33c in the direction MD, the smoothing process can be easily performed. Particularly, when the smoothed region 33a, 33b, 33c are provided in the length sufficiently greater than the width x of the tape 30, the fixed portion 30a of the tape 30 is certainly adhered on the smoothed region 33a, 33b, or 33c without offsetting out of the smoothed region in the direction MD. More particularly, when the smoothed region 33b is formed continuously over the entire length as shown in FIG. 5, positioning of the tape and the smoothed region becomes unnecessary.

Here, in the embodiment shown in FIGS. 1 to 3 and the embodiment shown in FIG. 4, the smoothed region is formed at a position inwardly offset from the strip form seal regions 25 and 26, in which the package sheets are bonded by heat seal at both side portions. Accordingly, area of the region of the package sheet 10 smoothed by heat treatment and the region formed into the film can be minimized. Thus, it becomes possible to restrict creation of husky or crinkly noise by friction of smoothed regions. Furthermore, since the package sheet 10 is not smoothed in the strip form seal regions 25 and 26 on both lateral sides, creation of husky or crinkly noise upon peeling the heat sealed portion in the strip form seal regions 25 and 26 can be restricted. Furthermore, since the smoothed regions are not located in the heat sealed regions, force required for peeling the heat seal in the strip form seal regions 25 and 26 can be made small to restrict creation of husky or crinkly noise.

On the other hand, in order to restrict the husky or crinkly noise of the package sheet, a width dimension X3 in the direction of MD in the region to be smoothed is preferably less than or equal to 80% of the width dimension in the direction of MD of the individual package. For instance, preferred width dimension of the region to be smoothed is less than or equal to 80 mm. On the other hand, a dimension Y3 of the region to be smoothed in the direction of CD is preferably less than or equal to 18 mm. It should be noted that the minimum area of the region to be smoothed is the area equal to the fixed region 31 of the tape 30.

Figure 7A:
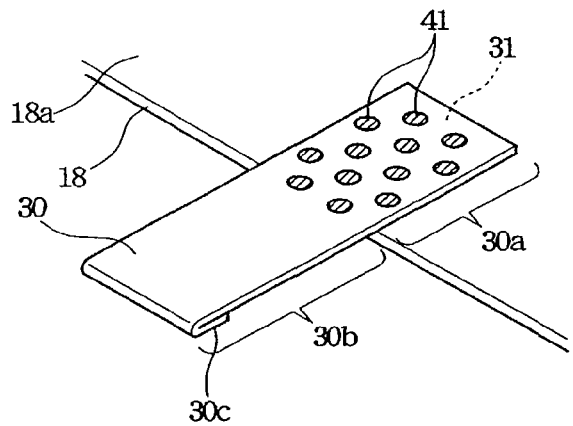
FIGS. 7A and 7B are partial perspective views of the individual package with other embodiments of the smoothed regions.
Figure 7B:
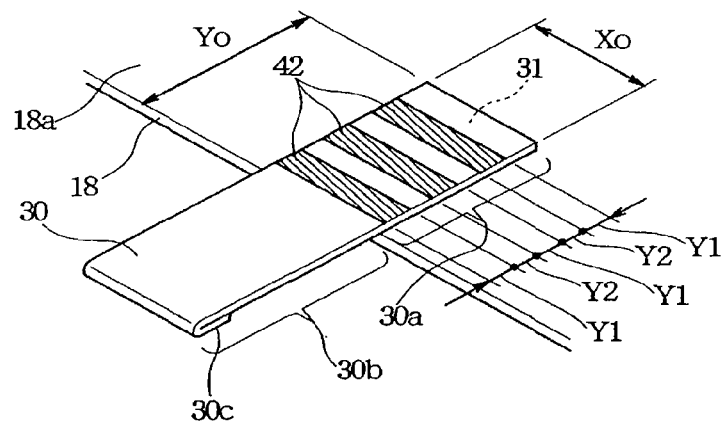

Next, as shown in FIGS. 7A and 7B, in the individual package 1, the surface 18a of the upper portion 18 of the package sheet 10 may be locally smoothed in the fixed region 31.

In the example shown in FIG. 7A, before adhering the fixed portion 30a of the tape 30 on the package sheet 10 or after adhering the fixed portion 30a of the tape 30 on the package sheet 10, the surface 18a of the package sheet 10 is pressurized by an emboss roll or pressurized and heated by the emboss roll to form dot form locally compressed portions 41. By the smoothing process, the surface 18a of the package sheet 10 is smoothed only in the locally compressed portions 41.

In the example shown in FIG. 7B, by the process similar to the above, strip form locally compressed portions 42 are formed. As a result, the surface 18a of the package sheet 10 is smoothed only in the locally compressed portions 42.

As set forth above, even when the surface 18a is locally smoothed in the fixed region 31, the smoothness of the fixed region 31 is preferably greater than or equal to 50% as set forth above, and is further preferably greater than or equal to 65%. On the other hand, when the package sheet 10 and the fixed portion 30a of the tape 30 are pressurized and heated together by an emboss roll to form the locally compressed portions 41 or 42 after fitting or fixing the fixed portion 30a of the tape 30 on the package sheet 10, the area ratio of the locally compressed portion relative to the fixed region 31 is preferably greater than or equal to 30%, and further preferably greater than or equal to 40%.

Figure 8:
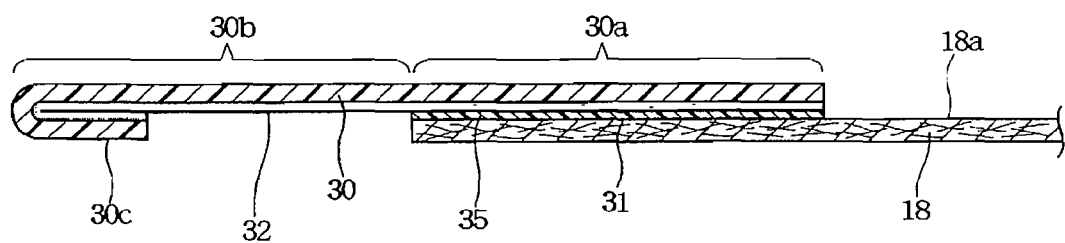
FIG. 8 is a partial section of the individual package showing adhering portion of a tape in another embodiment.

FIG. 8 is a partial section showing another embodiment of the present invention equivalent to FIG. 3B.

In the embodiment shown in FIG. 8, in the entire area of the fixed region 31 or a part thereof, a molten resin is coated and cured on the surface 18a of the upper portion 18 of the package sheet 10 to form a resin film 35 with flat surface. In the alternative, the resin film 35 may be formed by laminating a resin by melt extrusion laminating method.

Since the surface 18a of the package sheet 10 is smoothed by the resin film 35, the fixed portion 30a of the tape 30 is firmly adhered on the surface 18a by the pressure sensitive adhesive layer 32.

On the other hand, in this case, a strength required for peeling the resin film 35 from the surface of the package sheet 10 is preferably greater than or equal to 10N as converted into 25 mm width of the resin film 35 (i.e., 10N per 25 mm width of the resin film 35). When the strength is greater than or equal to 10N, upon pulling up the tape 30, unwanted peeling of the resin film 35, on which the fixed portion 30a of the tape 30 is adhered, from the surface 18a of the package sheet 10 can be successfully prevented.

It should be noted that, in the individual package 1 of the present invention, the package sheet 10 may be formed from a single layer of spun-bonded non-woven fabric, or a non-woven fabric fabricated by carding process, such as spun-laced non-woven fabric and so forth. In the alternative, the package sheet 10 may be formed from woven fabric.

On the other hand, the present invention is applicable for the package sheet formed of other materials as long as fibrous structure appears on the first surface 11 oriented outside of the individual package 1. For example, the package sheet 10 may be a composite sheet including non-woven fabric or woven fabric forming the first surface 11 and a resin film overlaid or coated on the second surface 12. In the alternative, the second surface may be formed by a resin film laminated on the back surface of the non-woven fabric or woven fabric by melt extrusion lamination process.

Figure 9:
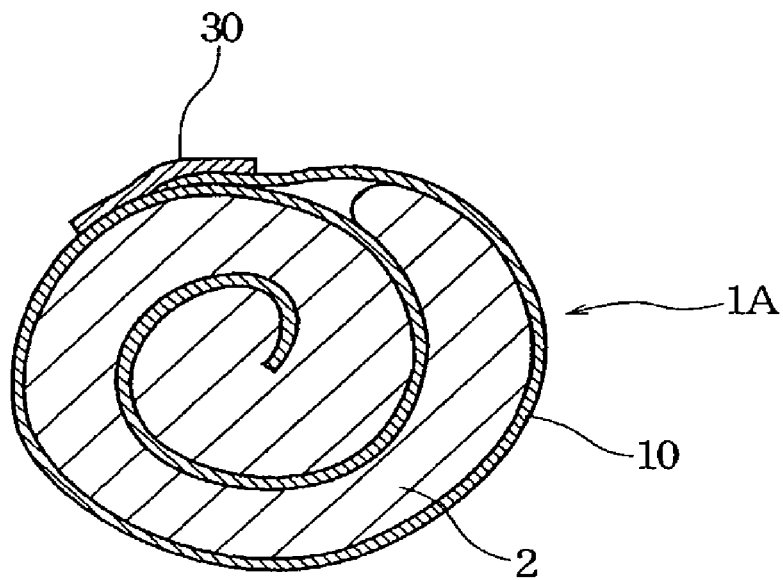
FIG. 9 is a section showing a further embodiment of the individual package according to the present invention.
Figure 10:
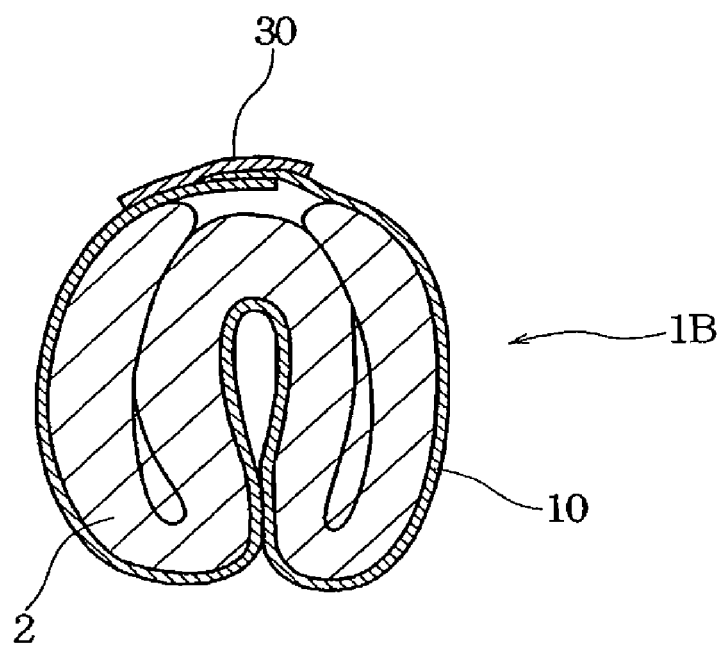
FIG. 10 is a section showing a still further embodiment of the individual package according to the present invention.

FIGS. 9 and 10 are sections showing other structures of individual packages.

In an individual package 1A shown in FIG. 9, the absorbent article such as sanitary napkin 2 and the package sheet 10 are packed in rolled form, and the package sheet 10 is fixed by the tape 30. In an individual package 1B shown in FIG. 10, the absorbent article such as sanitary napkin 2 and the package sheet 10 are folded into substantially W-shaped configuration. Even in this case, the package sheet 10 is fixed by the tape 30.

The smoothing process in the adhering portion between the fixed portion 30a of the tape 30 and the package sheet 10 in the present invention is applicable for the individual packages shown in FIGS. 9 and 10.

On the other hand, when the absorbent article to be packed is the sanitary napkin, the shape of the sanitary napkin may have no wing. The absorbent article is not specified to the sanitary napkin but can be panty liner, sanitary tampon, incontinence pad, disposable diaper and so forth.

EXAMPLE (1) Comparative Example

The package sheet 10 having a three-layer structure consisted of the spun-bonded non-woven fabric on the side of the first surface 11, the spun-bonded non-woven fabric on the side of the second surface 12, and a meltblown non-woven fabric sandwiched between the spun-bonded non-woven fabrics, having a basis weight of 18 g/m$^2$, and being not subject to smoothing process, was used.

(2) Example 1

The package sheet 10 having a three-layer structure consisted of the spun-bonded non-woven fabric on the side of the first surface 11, the spun-bonded non-woven fabric on the side of the second surface 12, and a meltblown non-woven fabric sandwiched between the spun-bonded non-woven fabrics, having a basis weight of 18 g/m$^2$, and being formed with a stripe form smoothed region 33a on the first surface 11, to which the tape 30 is bonded, as shown in FIG. 4, was used. The smoothing process was performed using a roll having a projected portion of a stripe pattern with smooth top surface, and a roll having smooth surface in entire periphery. Both rolls were heated to 115° C. The packager sheet 10 is pressurized by both rolls at a pressure of 36.3 kPa.

(3) Example 2

The package sheet 10 having a three-layer structure consisted of the spun-bonded non-woven fabric on the side of the first surface 11, the spun-bonded non-woven fabric on the side of the second surface 12, and a meltblown non-woven fabric sandwiched between the spun-bonded non-woven fabrics, having a basis weight of 15 g/m$^2$, and being formed with a stripe form smoothed region 33a is formed on the first surface 11, to which the tape 30 is bonded, as shown in FIG. 4, was used. The smoothing process was performed using a roll having a projected portion of a stripe pattern with smooth top surface, and a roll having smooth surface in entire periphery. Both rolls were heated to 105° C. The packager sheet 10 is pressurized by both rolls at a pressure of 36.3 kPa.

(4) Example 3

The package sheet 10 having a three-layer structure consisted of the spun-bonded non-woven fabric on the side of the first surface 11, the spun-bonded non-woven fabric on the side of the second surface 12, and a meltblown non-woven fabric sandwiched between the spun-bonded non-woven fabrics, having a basis weight of 15 g/m², and being formed with a stripe form smoothed region 33c on the first surface 11, to which the tape 30 is bonded, as shown in FIG. 6, was used. The smoothing process was performed using a roll having a projected portion of a stripe pattern with smooth top surface, and a roll having smooth surface in entire periphery. Both rolls were heated to 105° C. The packager sheet 10 is pressurized by both rolls at a pressure of 36.3 kPa.

(5) Example 4

The package sheet 10 having a three-layer structure having basis weight of 35 g/m² consisted of the spun-bonded non-woven fabric on the side of the first surface 11, the spun-bonded non-woven fabric on the side of the second surface 12, and a meltblown non-woven fabric sandwiched between the spun-bonded non-woven fabrics, further laminating a polyethylene film having a basis weight of 15.6 g/m² by extrusion on the first surface 11, to which the tape 30 is bonded, was used. The polyethylene film is formed of a mixture of LLDPE (linear low-density polyethylene and LDPE (low-density polyethylene) in a mass ratio of 7:3.

(6) Tape

The tape 30 is formed from a polypropylene film having a basis weight of 50 g/m². As shown in FIG. 11, a width X0 of the portion to be bonded to the package sheet 10 was 12.5 mm and a length Y0 thereof was 15 mm. The fixed portion 30a and the adhering portion 30b of the tape are applied a synthetic rubber type pressure sensitive bond in the basis weight of 15 g/m².

In the Comparative Example, the fixed portion 30a of the tape is bonded on the surface of the non-woven fabric, and in the Examples 1 to 3, the fixed portion 30a of the tape 30 is bonded on the smoothed region of the package sheet. On the other hand, in the Example 4, the fixed portion 30a of the tape 30 is bonded on the surface of the polyethylene film.

(7) Example 5

The package sheet 10 having a three-layer structure consisted of the spun-bonded non-woven fabric on the side of the first surface 11, the spun-bonded non-woven fabric on the side of the second surface 12, and a meltblown non-woven fabric sandwiched between the spun-bonded non-woven fabrics, having a basis weight of 18 g/m², was used. On the first surface 11 of the package sheet 10, the fixed portion 30a of the tape was bonded. The package sheet 10 and the fixed portion 30a were pressurized without heating to form the locally compressed portion 42 as shown in FIG. 7B. Strip form locally compressed portions 42 were formed at three positions. Size of each individual locally compressed portion 42 had a length Y1 of 2 mm and a width X0 of 12.5 mm. An interval Y2 between the locally compressed portions 42 was 3 mm.

An area ratio of the locally compressed portion versus the fixed region 31 was 40%.

(8) Smoothness

Smoothness of the surface of the non-woven fabric of the Comparative Example was measured, and with respect to the Examples 1, 2 and 3, smoothness of the smoothed portions were measured. The result of measurement is shown in the following table 1.

(9) Peel Strength Test

Figure 11A:
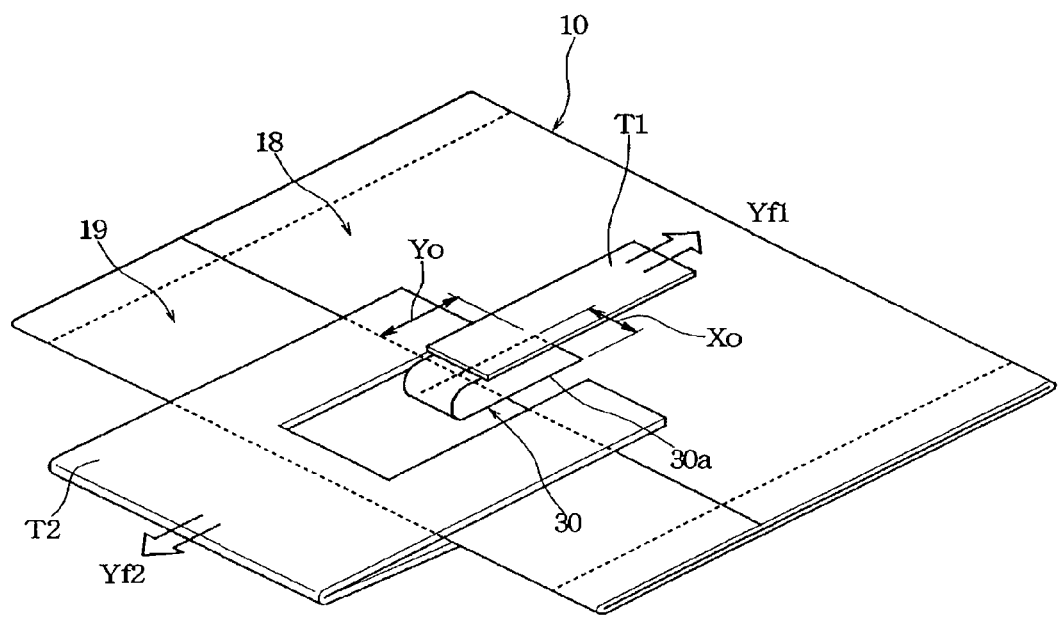
FIG. 11A is a perspective view for explaining an evaluation test.
Figure 11B:
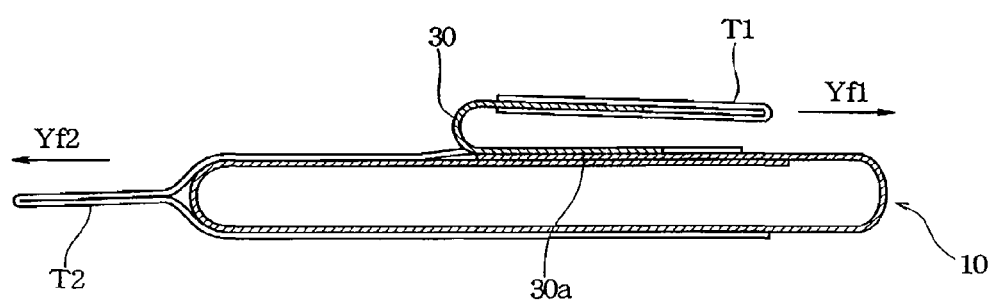
FIG. 11B is a section for explaining the evaluation test.

As shown in FIGS. 11A and 11B, at the tip end of the adhering portion 30b of the tape 30, a substantially non-expandable tape (gum tape) T1 was bonded, and a tape (gum tape) T2 was bonded over the entire package sheet 10. The tape T1 was pulled in a direction of Yf1 and the tape T2 was pulled in a direction of Yf2.

For measurement, an autograph "AGK-1kNG" manufactured by Shimazu Seisakusho Kabushiki Kaisha was used, and the tapes T1 and T2 are held with a distance between chucks. The chucks are moved away from each other at a speed 300 mm/min to measure a maximum force upon peeling the fixed portion 30a of the tape 30 from the package sheet. This is converted into a force (N) per a width of 25 mm.

(10) Package Opening Test

After leaving the Comparative Example and respective Examples under an environment of 4° C. for 6 hours, package opening test was performed by peeling the adhering portion 30b of the tape for 30 samples with respect to each Comparative Example and Example under environment of 4° C.

At this time, a number of the package sheets from which the fixed portions 30a are peeled off were counted. Evaluation was made to "◯" in the case where the counted number is 0 to 3, "Δ" in the case where the counted number is 4 to 15, and "x" in the case where the counted number is 15 to 30.

The results are shown in the table 1. In the table, a number of testers evaluated as "◯", "Δ" and "x" respectively are shown (It should be noted that the package opening test was performed by five testers).

TABLE 1

|  |  | C.Ex | Ex. 1 | Ex. 2 | Ex. 3 | Ex. 4 | Ex. 5 |
|---|---|---|---|---|---|---|---|
| Smoothness |  | 31.5% | 75.2% | 74.4% | 70.6% |  |  |
| Dot Area Ratio |  |  |  |  |  |  | 40% |
| Peel Strength (N/25 mm) |  | 5.94 | 10.44 | 17.38 | 15.8 | 17.66 | 15.04 |
| Package Opening Test | ◯ | 0 | 4 | 5 | 5 | 5 | 5 |
|  | Δ | 0 | 1 | 0 | 0 | 0 | 0 |
|  | x | 5 | 0 | 0 | 0 | 0 | 0 |

C.Ex: Comparative Example, Ex: Example

In the package of the present invention set forth above, the base end side of the tape can be firmly adhered to the package sheet. When the free end side of the tape is peeled off the surface of the package sheet, the package sheet of the individual package can be easily unpacked.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

The invention claimed is:

1. A method for manufacturing an individual package of an absorbent article, wherein said absorbent article is wrapped by a package sheet formed from a non-woven fabric of thermoplastic fibers and has mutually opposing side edge portions and mutually opposing end edges, one end edge being overlapped over the other end edge by placing said one end edge of said package sheet outside for forming an overlapping portion, and said package sheet is releasably sealed along said side edge portions, wherein a base end of a tape is fixed on the surface of said package sheet located outside in said overlapping portion to form a fixed region, wherein a free end of said tape extends across said one end edge and is releasable adhered on the outer surface of said package sheet adjacent said one end edge, and wherein said package sheet has a surface for fixedly receiving said base end of said tape, the method comprising the steps of smoothing said surface for fixedly receiving said base end of said tape in said fixed region by heating and pressurizing one or more of the thermoplastic fibers to form a film, forming a pressure-sensitive adhesive layer on a lower surface of said tape along at least said base end and said free end of said tape, and bonding said side edge portions of said package sheet in a plurality of layers with each other, wherein said surface smoothed by said smoothing step includes at least said fixed region and is formed at said one end edge of the package sheet within the overlapping portion, and wherein said surface smoothed by said smoothing step is located at a position away from the bonded portion of said package sheet.

2. A method for manufacturing an individual package of an absorbent article as set forth in claim 1, wherein said surface smoothed by said smoothing step extends beyond said fixed region.

* * * * *